United States Patent
Shuto et al.

[11] Patent Number: 5,865,771
[45] Date of Patent: Feb. 2, 1999

[54] INCUBATOR MAT APPARATUS WITH SOUND GENERATOR

[75] Inventors: Toshio Shuto, Saitama-ken; Tatuhiko Seki, Honjo; Kazuo Matubara, Tokyo, all of Japan

[73] Assignee: Atom Medical Corporation, Tokyo, Japan

[21] Appl. No.: 784,444

[22] Filed: Jan. 16, 1997

[30] Foreign Application Priority Data

Jan. 31, 1996 [JP] Japan ................................. 8-037283

[51] Int. Cl.$^6$ ........................... A61H 1/00; A61M 21/00
[52] U.S. Cl. ................................ 601/47; 601/57; 5/904; 600/28
[58] Field of Search ................... 601/47, 49, 56, 601/57, 58–61, 65, 69, 70; 5/904; 600/28

[56] References Cited

U.S. PATENT DOCUMENTS

| | | | |
|---|---|---|---|
| 4,757,548 | 7/1988 | Fenner | 601/47 X |
| 4,967,871 | 11/1990 | Komatsubara | 601/47 X |
| 5,007,410 | 4/1991 | DeLaney | 601/53 |
| 5,035,235 | 7/1991 | Chesky | 601/47 |
| 5,063,912 | 11/1991 | Hughes | 601/47 |
| 5,442,710 | 8/1995 | Komatsu | 601/47 X |
| 5,464,381 | 11/1995 | Wilson | 601/49 |

FOREIGN PATENT DOCUMENTS

| | | |
|---|---|---|
| 1-277563 | 11/1989 | Japan . |
| 4-371153 | 12/1992 | Japan . |
| 6-38821 | 5/1994 | Japan . |
| 7-102219 | 11/1995 | Japan . |

*Primary Examiner*—Danton D. DeMille
*Attorney, Agent, or Firm*—Woodcock Washburn Kurtz Mackiewicz & Norris LLP

[57] ABSTRACT

Electromechanical vibration transducers are embedded in a pad, and a mat on which a newborn baby is placed is stacked on the pad. A graphic equalizer is arranged to correct the frequency characteristics of a sound signal generated by a sound signal generator to characteristics close to the original frequency characteristics even if sounds are reflected to interfere with each other in an incubator. Comfortable vibrations can be applied to the newborn baby. In addition, sounds having frequency characteristics close to the original frequency characteristics can be played for the newborn baby. The newborn baby therefore can feel at ease, and at the same time bedsores, night terrors, and the like can be prevented. Maintenance cost is also low.

2 Claims, 2 Drawing Sheets

INCUBATOR MAT APPARATUS WITH SOUND GENERATOR

BACKGROUND OF THE INVENTION

1. Field of the Invention

The present invention relates to an incubator mat apparatus including a mat placed in an incubator for housing a newborn baby.

2. Description of the Prior Art

FIG. 1 shows an incubator 11 for housing a newborn baby to prevent a body temperature drop or the like. A mat 12 in which an urethane foam or the like is filled and on which a newborn baby is to be placed is placed in the incubator 11. An openable transparent hood 13 is mounted on the incubator 11 so that the temperature, humidity, and the like in the incubator are kept constant to prevent the body temperature drop of the newborn baby and the newborn baby can be observed.

In recent years, in order to make a newborn baby feel at ease to prevent night terrors, intrauterine sounds, music, and the like are played for newborn babies. Compact disks on which these sound sources are recorded are commercially available.

When the intrauterine sounds, music, and the like are generated in the incubator 11 closed with the hood 13, the intrauterine sounds, music, and the like are reflected in the incubator 11 to interfere with each other. As a result, a sound having a specific frequency becomes loud, and a sound having another specific frequency becomes faint.

As a result, the frequency characteristics of the intrauterine sounds, music, and the like are deviated from the original frequency characteristics. The newborn baby rather feels uncomfortable. It is therefore difficult to pursue the initial purpose for making the newborn baby feel at ease to prevent night terrors or the like.

OBJECT AND SUMMARY OF THE INVENTION

It is, therefore, an object of the present invention to provide an incubator mat apparatus capable of playing intrauterine sounds, music, and the like having frequency characteristics close to the original frequency characteristics for a newborn baby and at the same time giving comfortable vibrations to the newborn baby to prevent night terrors and the like by making the newborn baby feel at ease and by preventing the bedsore of the newborn baby even if an incubator is closed for keeping the temperature, humidity, and the like constant, and, in addition, having a low maintenance cost.

An incubator mat apparatus according to the present invention is characterized by comprising a pad in which an electromechanical vibration transducer is embedded, a mat stacked on the pad to place a newborn baby thereon, and a graphic equalizer for correcting frequency characteristics of a sound signal supplied to the electromechanical vibration transducer.

Since the electromechanical vibration transducer is embedded in the pad, sound signals such as intrauterine sounds, music, and the like are converted into coenesthetic acoustic vibrations to give comfortable vibrations to the newborn baby through the mat. In addition, the frequency characteristics of the sound signal supplied to the electromechanical vibration transducer can be corrected by the graphic equalizer. Even if the incubator is closed with the hood to keep the temperature, humidity, and the like constant, and the sounds are reflected to interfere with each other in the incubator, the intrauterine sounds, music, and the like having frequency characteristics close to the original frequency characteristics can be played for the newborn baby. Therefore, the newborn baby can feel at ease, and at the same time the bedsore of the newborn baby can be prevented, thereby preventing night terrors or the like.

The pad in which the electromechanical vibration transducer is embedded and the mat on which the newborn baby is placed are constituted by separate members. Even if the mat is contaminated or damaged, the pad in which the electromechanical vibration transducer is embedded can be continuously used. Only the inexpensive mat can be replaced with a new one. Therefore, the maintenance cost is lower than a case in which the mat and pad are replaced with new ones.

An incubator mat apparatus according to the present invention preferably comprises a sound signal generator for generating the sound signal and a speaker amplifier for amplifying the sound signal whose frequency characteristics are corrected and supplying an amplified sound signal to the electromechanical vibration transducer. With this arrangement, comfortable vibrations can be applied to the newborn baby, and intrauterine sounds, music, and the like having the frequency characteristics close to the original frequency characteristics can easily be played for the newborn baby. Therefore, the night terrors and the like of the newborn baby can be easily prevented.

DETAILED DESCRIPTION OF THE PREFERRED EMBODIMENT

Figure 1:
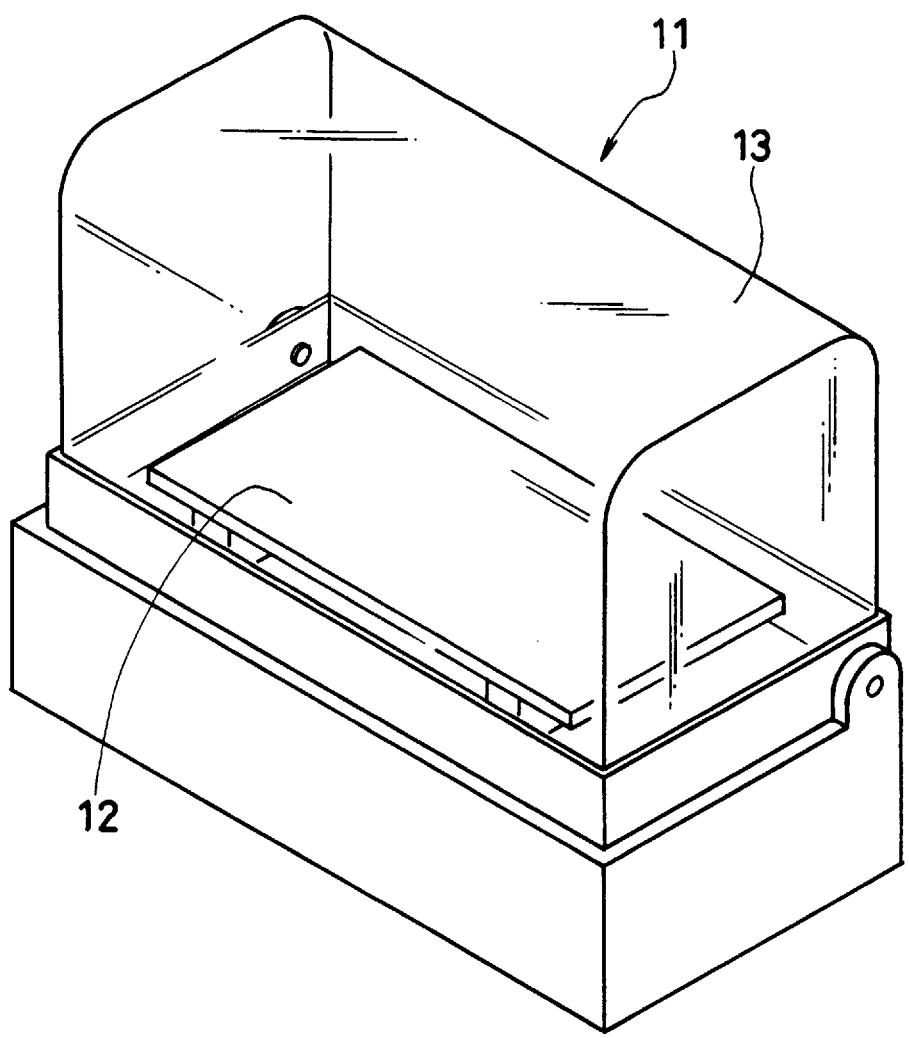
FIG. 1 is a perspective view of an incubator to which an incubator mat apparatus according to an embodiment of the present invention can be applied.

An embodiment of the present invention will be described below with reference to FIGS. 1 and 2. As shown in FIG. 2, an incubator mat apparatus 21 of the embodiment has a lower pad 23 in which a plurality of electromechanical vibration transducers 22 for mainly converting low-frequency components of a sound signal into coenesthetic acoustic vibrations are embedded, and an upper mat 24 filled with an urethane foam or the like and placed on the pad 23. A newborn baby is to be placed on the upper mat 24.

A sound signal generator 25 such as a compact disk player or a tape player is arranged. A graphic equalizer 26 for correcting the frequency characteristics of the sound signal is connected to the sound signal generator 25. A speaker amplifier 27 for amplifying the sound signal is connected to the graphic equalizer 26. The electromechanical vibration transducers 22 are connected to the speaker amplifier 27.

Figure 2:
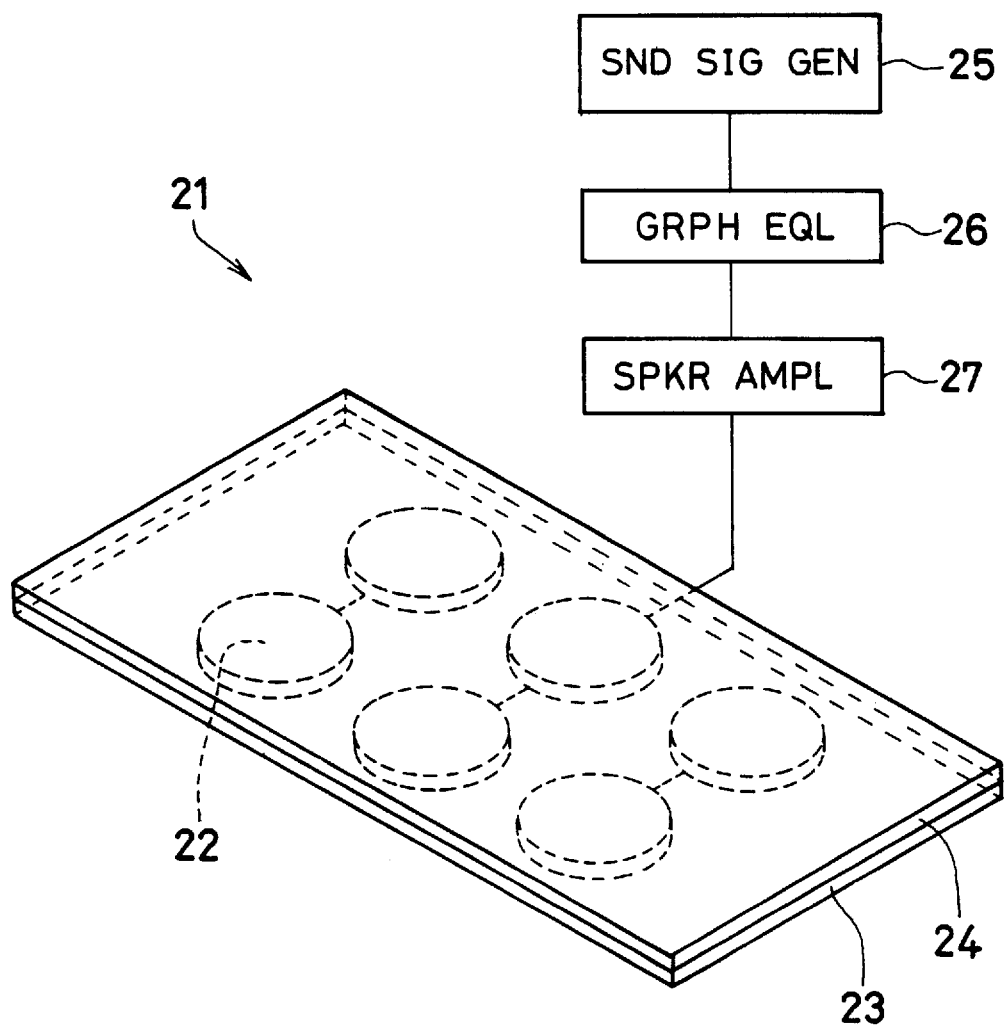
FIG. 2 is a view showing the concept of the embodiment of the present invention.

In use of the incubator mat apparatus 21 of this embodiment described above, the pad 23 and the mat 24 are placed in the incubator 11 in place of the mat 12 of the prior art shown in FIG. 1.

The frequency characteristics of the sound signal such as intrauterine sounds, music and the like generated by the sound signal generator 25 are corrected by the graphic equalizer 26 to sounds having frequency characteristics close to the original frequency characteristics even if the sounds are reflected to interfere with each other in the incubator 11 closed with the hood 13. More specifically, a sound having a frequency which becomes loud due to the interference is made faint, while a sound having a frequency which becomes faint due to the interference is made loud.

The sound signal whose frequency characteristics are corrected by the graphic equalizer 26 is amplified by the speaker amplifier 27. The amplified sound signal is supplied to the electromechanical vibration transducers 22. The comfortable coenesthetic acoustic vibrations generated by the electromechanical vibration transducers 22 are applied to the newborn baby on the mat 24 through the mat 24. At the same time, the sounds such as intrauterine sounds, music, and the like having frequency characteristics close to the original frequency characteristics can be played for the newborn baby.

When the coenesthetic acoustic vibrations are applied to the newborn baby as described above, the newborn baby itself vibrates due to its light weight, thereby preventing the bedsore of the newborn baby. When the intrauterine sounds, music, and the like having the frequency characteristics close to the original frequency characteristics are played for the newborn baby, the newborn baby can feel at ease in addition to the comfortable coenesthetic acoustic vibrations. Therefore, this makes it possible to effectively prevent the night terrors of the newborn baby.

As can be apparent from FIG. 2, the pad 23 in which the electromechanical vibration transducers 22 are embedded and the mat 24 on which the newborn baby is placed are constituted by separate members. Even if the mat 24 is contaminated or damaged by placing the newborn baby thereon, the pad 23 in which the electromechanical vibration transducers 22 are embedded can be continuously used, and only the inexpensive mat 24 can be replaced with a new one.

The entire surfaces of the pad 23 and the mat 24 may be covered with a waterproof cover (not shown). In this case, contamination and damage to the pad 23 and the mat 24, and particularly the pad 23 in which the electromechanical vibration transducers 22 are embedded can be prevented. Therefore, necessity for replacement of the pad 23 can be reduced.

What is claimed is:

1. An mat apparatus for use in an incubator characterized by comprising:

a pad in which an electromechanical vibration transducer is embedded;

a mat stacked on said pad to place a newborn baby thereon;

a sound signal generator for generating a sound signal; and a graphic equalizer for correcting frequency characteristics of the sound signal supplied to said electromechanical vibration transducer so that the frequency characteristics turn into original frequency characteristics after sounds are reflected to interfere with each other in an incubator.

2. An apparatus according to claim 1, characterized by further comprising:

a speaker amplifier for amplifying the sound signal whose frequency characteristics are corrected and supplying an amplified sound signal to said electromechanical vibration transducer.

* * * * *